(12) United States Patent
Naylor et al.

(10) Patent No.: US 11,628,332 B2
(45) Date of Patent: Apr. 18, 2023

(54) ORAL TRAINING DEVICE

(71) Applicant: Sonaids Limited, Southport (GB)

(72) Inventors: Peter Naylor, Southport (GB); Philip Sutton, Southport (GB)

(73) Assignee: SONAIDS Limited, Southport (GB)

( * ) Notice: Subject to any disclaimer, the term of this patent is extended or adjusted under 35 U.S.C. 154(b) by 238 days.

(21) Appl. No.: 16/920,617

(22) Filed: Jul. 3, 2020

(65) Prior Publication Data

US 2021/0008409 A1   Jan. 14, 2021

(30) Foreign Application Priority Data

Jul. 8, 2019   (GB) ...................................... 1909787

(51) Int. Cl.
| | | |
|---|---|---|
| *A63B 23/03* | (2006.01) | |
| *A63B 21/00* | (2006.01) | |
| *A63B 21/02* | (2006.01) | |
| *A61F 5/56* | (2006.01) | |

(52) U.S. Cl.
CPC .......... *A63B 23/032* (2013.01); *A63B 21/028* (2013.01); *A63B 21/4035* (2015.10); *A61F 5/56* (2013.01); *A63B 2209/00* (2013.01)

(58) Field of Classification Search
CPC ...... A61F 5/56; A61F 5/566; A63B 21/00185; A63B 21/002; A63B 21/0023; A63B 21/028; A63B 21/04; A63B 21/0442; A63B 21/4003; A63B 21/4035; A63B 21/4039; A63B 23/03; A63B 23/032; A63B 23/18; A63B 71/085; A63B 2071/088; A63B 2209/00; A63B 2214/00
See application file for complete search history.

(56) References Cited

U.S. PATENT DOCUMENTS

| | | | | |
|---|---|---|---|---|
| 3,805,771 A | * | 4/1974 | Wright ..................... | A61C 7/00 482/11 |
| 5,313,960 A | * | 5/1994 | Tomasi .................... | A61F 5/566 128/862 |
| 5,320,114 A | * | 6/1994 | Kittelsen .............. | A61C 17/036 128/861 |
| 5,431,610 A | * | 7/1995 | Miller .................. | A63B 23/032 482/122 |
| 5,662,554 A | * | 9/1997 | Schaefer ............ | A63B 21/4003 482/10 |

(Continued)

FOREIGN PATENT DOCUMENTS

| | | |
|---|---|---|
| EP | 3530230 A1 | 8/2019 |
| JP | 2016189937 A | 11/2016 |
| JP | 2019025135 A | 2/2019 |

*Primary Examiner* — Gary D Urbiel Goldner
(74) *Attorney, Agent, or Firm* — Craft Chu PLLC; Andrew W. Chu

(57) ABSTRACT

The oral training device for muscles of the throat and/or face includes a panel which is receivable in the oral cavity formed between the lips and teeth. The panel has a first face adjacent to the lip area and an opposite second face being adjacent to the teeth and/or gums when in use. The device includes a handle which projects outwardly from the first face for applying an outward pulling force to the panel generally away from the oral cavity. The device also includes an elongate platform extending laterally across the first face onto which the upper and lower lips are placeable when in use.

12 Claims, 2 Drawing Sheets

(56) References Cited

U.S. PATENT DOCUMENTS

| | | | |
|---|---|---|---|
| D754,865 S * | 4/2016 | Hägg | A63B 21/4003 |
| | | | D24/200 |
| 9,895,575 B2 * | 2/2018 | Hagg | A61B 5/682 |
| 2006/0122036 A1 * | 6/2006 | Ferrara | A63B 21/02 |
| | | | 482/121 |
| 2009/0188510 A1 * | 7/2009 | Palmer | A61F 5/566 |
| | | | 128/848 |
| 2011/0264017 A1 * | 10/2011 | Smernoff | A61H 1/02 |
| | | | 601/38 |
| 2013/0130193 A1 * | 5/2013 | Fisher | A61C 7/08 |
| | | | 269/46 |
| 2013/0296751 A1 * | 11/2013 | Martin | A61F 7/03 |
| | | | 601/148 |
| 2014/0007868 A1 * | 1/2014 | Eaton | A61B 13/00 |
| | | | 128/200.26 |
| 2016/0030802 A1 * | 2/2016 | Hagg | A61B 5/224 |
| | | | 482/10 |
| 2018/0207475 A1 * | 7/2018 | Djupvik | A63B 21/00185 |
| 2019/0046301 A1 * | 2/2019 | Lovat | A61C 9/0006 |
| 2021/0000674 A1 * | 1/2021 | Ramalho Da Fonseca | |
| | | | A61B 1/24 |

* cited by examiner

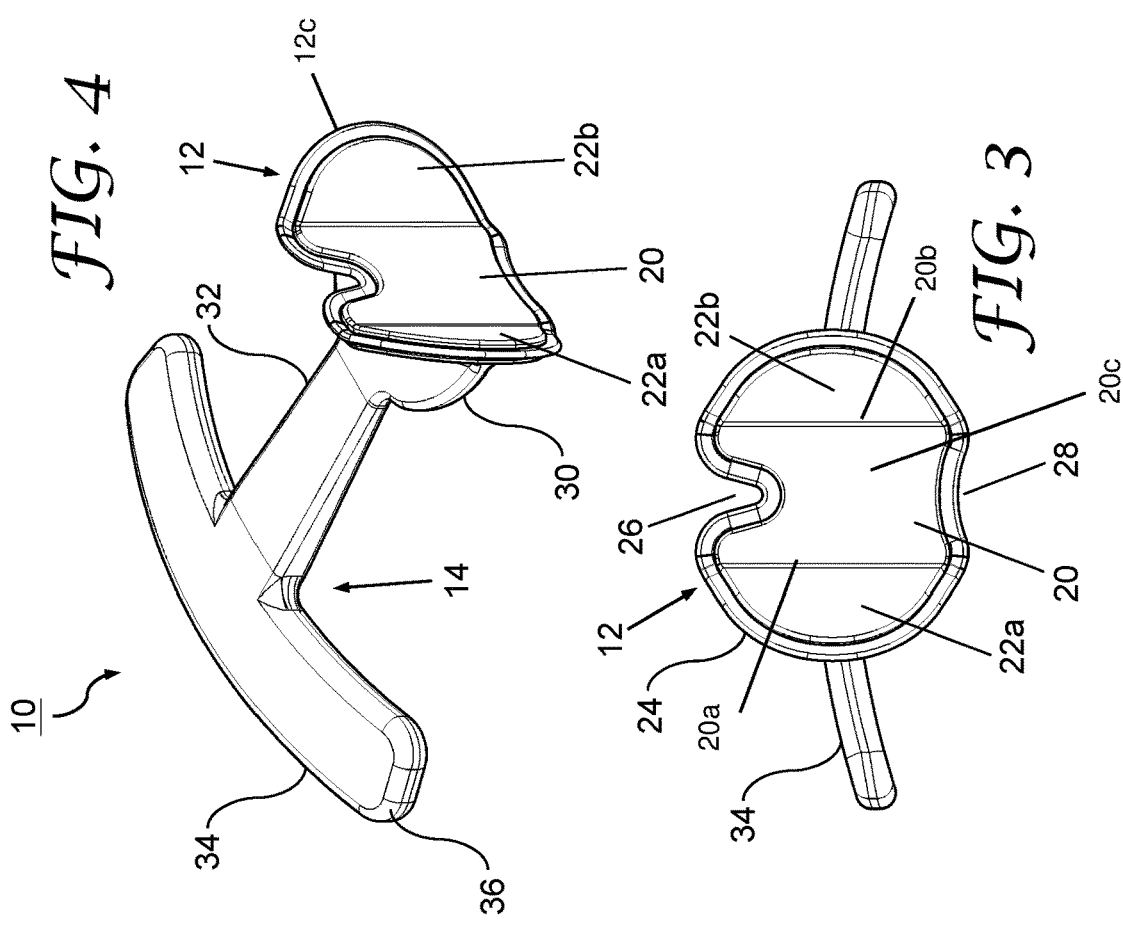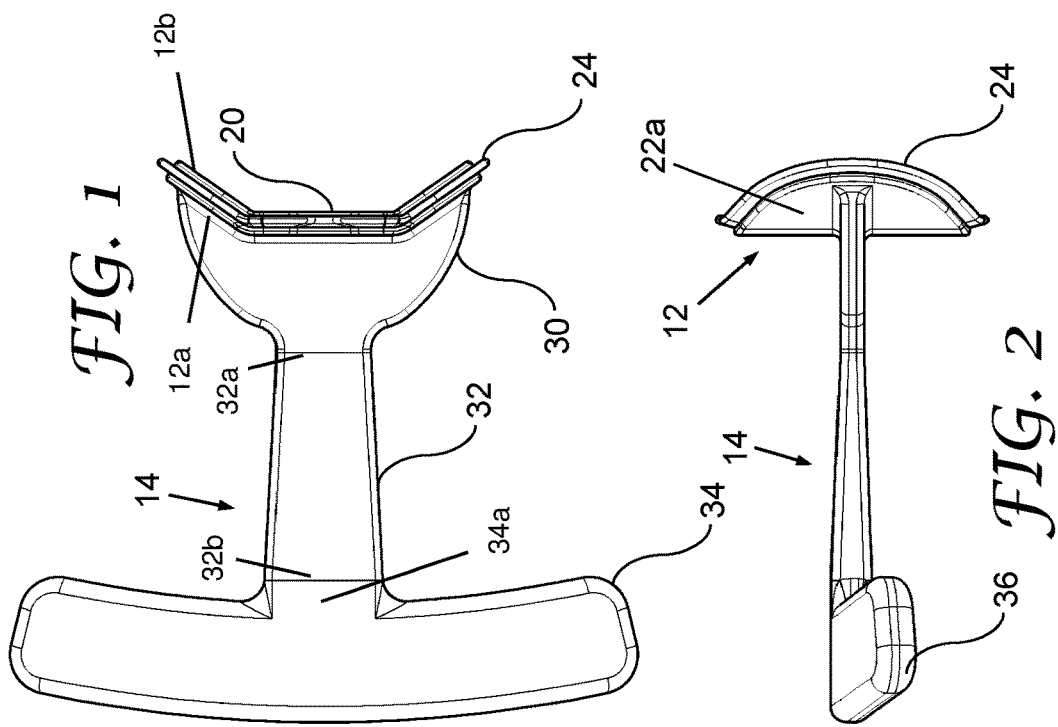

ORAL TRAINING DEVICE

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

This invention relates to an oral training device. In particular, the present invention relates to an oral training device that can be used to strengthen or train the muscles of the throat, mouth and lips in order to alleviate or cure snoring. The oral training device being a simple and effective device that can be used with very little instruction, and with minimal effort and time commitment, and yet provides very effective results.

2. Description of Related Art Including Information Disclosed Under 37 CFR 1.97 and 37 CFR 1.98

Products to help reduce snoring usually require the snoring sufferer to use something throughout the night, which is often uncomfortable and unsightly. The more severe options themselves can be noisy and disruptive to a snoring sufferer's sleep. None of these products have found real traction in the marketplace, or have enjoyed any real commercial success, for a number of reasons.

It is widely accepted that snoring occurs when a sufferer cannot move air freely through their nose and throat when sleeping. This makes the surrounding tissues vibrate, and which produces the characteristic snoring sound. Sufferers often have too much throat and nasal tissue or floppy or untrained tissue that is more prone to vibrate. Snoring can disrupt the quality of sleep leading to daytime fatigue, irritability and other health problems. Snoring often disrupts a partner's sleep as well, which can lead to relationship issues. If untreated, snoring can develop into more dangerous conditions, including sleep apnoea.

It is also widely accepted that as well as nasal and sinus problems, lifestyle factors including alcohol, smoking and use of certain medications can all exasperate snoring. Other lifestyle factors, which include being overweight or out of shape and age can have a significant impact on snoring since fatty tissue and poor muscle tone around the throat, mouth and lips unquestionably contribute to snoring. Sometimes exercise and diet can be all that is needed to reduce snoring problems.

There have been several products that have purported to produce significant improvements in terms of repairing muscular function and swallowing capacity in stroke patients, however none of them have specifically addressed the condition of snoring which is a major problem for sufferers and their partners.

It is an object of the present invention to provide an oral training device that better addresses the widespread problem of snoring by providing an oral training device that can be used to improve the muscle tone in the throat, mouth and lips. It is a further object of the present invention to provide a device that can significantly alleviate or cure snoring by strengthening or training the muscles of the throat, mouth and lips through a simple and effective exercise that yields substantial improvements in a relatively short timeframe. The shape of the device being such that it maximises the pressure applied to the anterior mouth/lip area and which has been found to produce a very beneficial effect.

BRIEF SUMMARY OF THE INVENTION

The present invention is described herein and in the claims.

According to the present invention there is provided an oral training device for training the muscles of the throat and/or face, comprising:
- a panel which is receivable in the oral cavity formed between the lips and teeth, the panel having a first face being adjacent to the lip area and an opposite second face being adjacent to the teeth and/or gums when in use;
- a handle which projects outwardly from the first face for applying an outward pulling force to the panel generally away from the oral cavity; and
- an elongate platform extending laterally across the first face onto which the upper and lower lips are placeable when in use.

An advantage of the present invention is that it can be easily and reproducibly used to maximise the pressure applied to the anterior mouth/lip area to produce an enhanced muscle training effect of the mouth and pharynx to alleviate or cure snoring.

Preferably, the panel being formed having a truncated V-shape when in plan view from above, and being divided into three generally flat walls.

Further preferably, the panel comprises:
- a centrally disposed wall which when the panel is received in the oral cavity being proximate to the central/lateral incisors in the upper and lower jaws; and
- lateral walls positioned either side of the centrally disposed wall which when the panel is received in the oral cavity being proximate to the lateral incisors/canine teeth in the upper and lower jaws.

In use, each of the lateral walls may be offset from the surface of the centrally disposed wall by an angle in the range of approximately 30° to approximately 40°.

Preferably, each of the lateral walls being offset from the surface of the centrally disposed wall by an angle in the range of approximately 35°.

Further preferably, the outer periphery of the panel further comprises:

an upper cut-out disposed in the centrally disposed wall which in use receives the upper or superior labial frenulum of the user; and a lower cut-out disposed in the centrally disposed wall which in use receives the lower or inferior labial frenulum of the user.

In use, the panel may be dimensioned such that the outward pulling force is applied to the anterior mouth and/or lip area proximate to the anterior parts of the generally horseshoe-shaped upper and lower jaws.

Preferably, the panel having a greater width than height and having a generally asymmetrical Booth lemniscate shape.

Further preferably, the device comprises a peripheral ridge being situated around the periphery of the panel.

In use, the peripheral ridge may have a reduced wall thickness between the first face and second face of the panel.

Preferably, the peripheral ridge being deformable to seal the plate within the oral cavity of the user.

Further preferably, the elongate platform being adapted to act as a base or ledge onto which the upper and lower lips can be pursed when in use.

In use, the elongate platform being generally crescent-shaped when in plan view from above.

Preferably, the handle further comprises:

an outwardly projecting arm which extends in a plane normal to the centrally disposed wall and having a first end being proximate to the elongate platform; and an elongate grip being positioned orthogonally to the arm and being connected at its midpoint to the opposite second end of the arm.

Further preferably, the length of the elongate grip is at least 1.5 times greater than the width of the lateral walls positioned either side of the centrally disposed wall.

In use, the device may be resiliently deformable and being formed from a semi-pliable polymer material.

Preferably, the device is integrally formed via injection moulding and/or blow moulding and/or vacuum forming and/or rotational moulding and/or compression moulding and/or rim moulding and/or powder impression moulding and/or any form of plastics or rubber manufacture.

Also according to the present invention there is provided a method of training the muscles of the throat and/or face in order to alleviate or cure snoring, the method of comprising the steps of:

inserting an oral training device comprising a handle at one end thereof and a panel at the opposite second end thereof into the mouth between the lips and teeth;

closing the mouth around the panel of the oral training device and pressing the lips around a lip platform formed with the handle without the teeth biting;

pulling the handle of the device outwards generally away from the mouth and holding the lips shut in order to resist the panel from leaving the mouth; and holding this configuration for between around five seconds to around ten seconds.

Preferably, the steps of inserting, closing, pulling and holding form a muscle training exercise which is repeated three to five times with a rest between each completed muscle training exercise.

Further according to the present invention there is provided a method of manufacturing an oral training device as hereinbefore described, comprising the steps of:

supplying a polymer into a moulding tool which defines the shape of the oral training device and having a polished surface finish; and ejecting the moulded device from the moulding tool.

Preferably, the polymer is a food grade polymer.

Further preferably, the polymer is selected from the group consisting, but not limited to, any of the following: Low-Density Polyethylene (LDPE), Polypropylene (PP), High-Density Polyethylene (HDPE), Polyethylene Terephthalate (PET), Polyvinyl Chloride (PVC) or Acrylonitrile Butadiene Styrene (ABS) or blends thereof.

In use, the method may further comprise a step of admixing an antimicrobial additive with the polymer.

Preferably, the antimicrobial additive comprises an active ingredient based on silver ions.

Further preferably, the method may further comprise a step of admixing one or more dyes or pigment with the polymer.

It is believed that an oral training device, its method of use and its method of manufacture in accordance with the present invention at least addresses the problems outlined above.

It will be obvious to those skilled in the art that variations of the present invention are possible and it is intended that the present invention may be used other than as specifically described herein.

BRIEF DESCRIPTION OF THE SEVERAL VIEWS OF THE DRAWINGS

The present invention will now be described by way of example only, and with reference to the accompanying drawings.

FIG. 1 illustrates a plan view from above of the oral training device of the present invention.

FIG. 2 shows an elevation view from the side of the oral training device of FIG. 1.

FIG. 3 is an elevation view from the rear of the oral training device of FIG. 1.

FIG. 4 illustrates a side perspective view from above and the rear of the oral training device of FIG. 1.

DETAILED DESCRIPTION OF THE INVENTION

The present invention has adopted the approach of addressing the widespread problem of snoring by providing an oral training device that can be used to improve the muscle tone in the throat, mouth and lips. Advantageously, the present invention provides a device that can significantly alleviate or cure snoring by strengthening or training the muscles of the throat, mouth and lips through a simple and effective exercise that yields substantial improvements in a relatively short timeframe. The shape of the device being such that it maximises the pressure applied to the anterior mouth/lip area and which has been found to produce a very beneficial effect.

Figure 6:
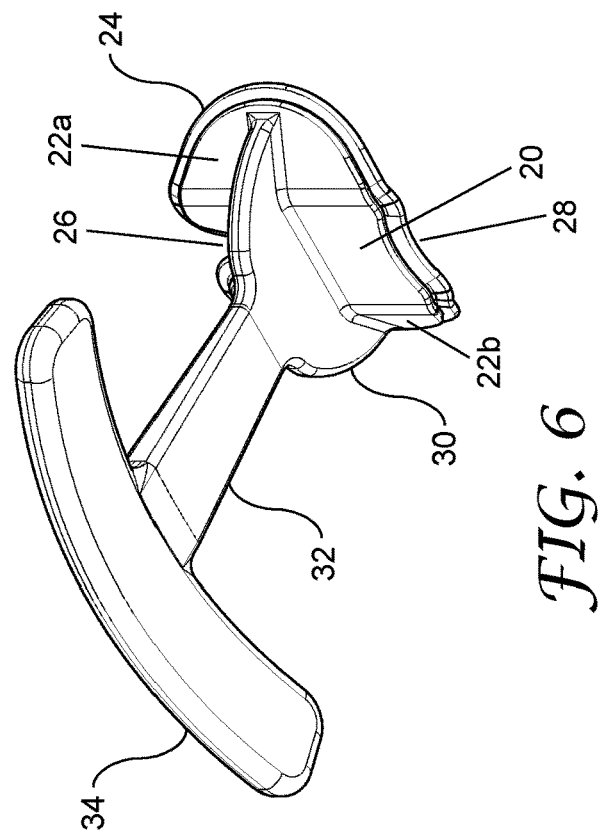
FIG. 6 is a side perspective view from below and the front of the oral training device of FIG. 1.
Figure 5:
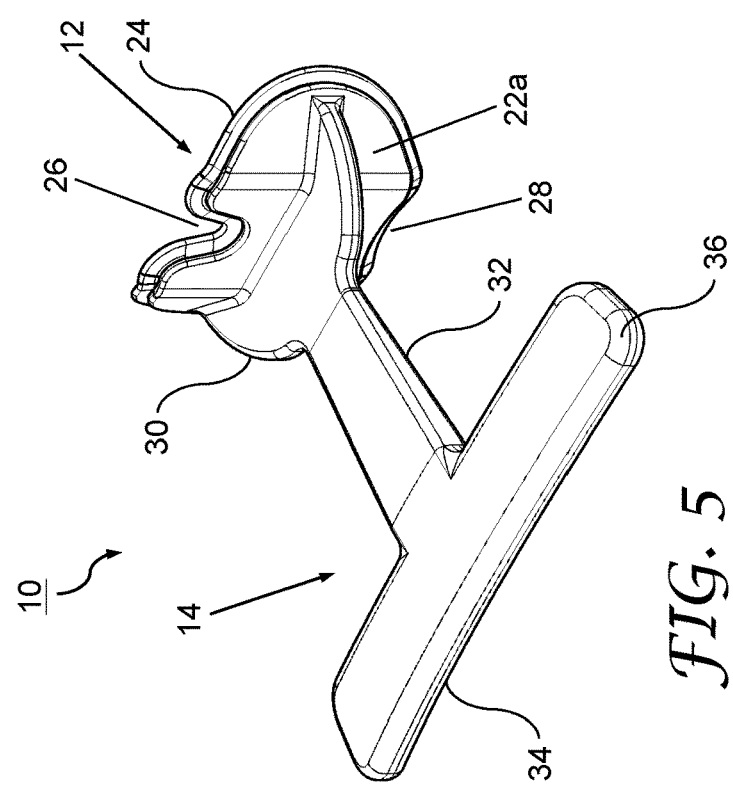
FIG. 5 shows a side perspective view from above and the front of the oral training device of FIG. 1.

Referring now to the drawings, an oral training device 10 according to the present invention is illustrated in FIGS. 1 to 6. The oral training device 10 comprises a plate or panel 12 that in use is received inside the mouth and placed behind the lips and in front of the teeth of a user. The panel 12 being connected to a pulling handle 14 which is used to apply a pulling force on the anterior mouth/lip area when in use. The device 10 is specifically designed to assist a user who is a snoring sufferer. However, the skilled person will understand that the term "user" (that is, a person who grasps the handle 14 of the device 10 and places the panel 12 in their own oral cavity) could also be two different people, namely a "recipient" (that is a person who wishes to improve the muscle tone in the throat, mouth and lips, but may not have the necessary motor skills or strength to operate the device 10 independently), and as such the use of the device 10 can be administered on a such a recipient by another person, such as a "caregiver" or the like.

The panel 12 has a greater width than its height and has a generally asymmetrical Booth lemniscate shape when in plan view from the front or rear, and as perhaps best shown in FIG. 3.

The panel 12 when in plan view from above, and as best shown in FIG. 1, is formed having a truncated V-shape, such that it is divided up into three generally flat walls 20, 22a, 22b. The panel 12 comprises a first face 12a, a second face 12b opposite the first face 12a, an outer periphery 12c, a centrally disposed wall 20 which, when the panel 12 is inserted into the oral cavity behind the lips and in front of the teeth of the user, would be adjacent to the central/lateral incisors in the upper and lower jaws. Positioned either side (first side 20a, second side 20b) of the centre wall 20 is a left lateral wall 22a on the first side 20a and a right left lateral wall 22b on the second side 20b. The lateral walls 22a, 22b which, when the panel 12 is inserted into the oral cavity behind the lips and in front of the teeth of the user, would be adjacent to the lateral incisors/canine teeth in the upper and lower jaws. The panel 12 being dimensioned such that a pulling force can be applied to the anterior mouth/lip area being adjacent to the outermost parts of the horseshoe-shaped upper (maxilla) and lower (mandible) jaws.

Advantageously, each of the lateral walls 22a, 22b being offset from the surface 20c of the centrally disposed wall 20 by an angle in the range of 30° to 40°. More preferably, the lateral walls 22a, 22b are each at an angle of approximately 35° to the surface 20c of the centrally disposed wall 20.

Situated around the periphery of the panel 12 is a peripheral ridge 24. In use, this thinner-dimensioned outer boundary or ridge 24 allows liquid/saliva within the oral cavity of the user to create a greater vacuum and thus increasing the effectiveness of the device 10 on the user, as is described in further detail below.

The outer periphery 12c of the panel 12 and the peripheral ridge 24 includes an upper cut-out 26 which in use can receive the upper or superior labial frenulum which joins the upper lip to the gum of the user. Equally, a second cut-out 28 is provided in the lower part of the panel 12 and peripheral ridge 24 which in use can receive the lower or inferior labial frenulum which joins the lower lip to the gum of the user.

Positioned along a centreline across the widest part of the panel 20 and proximate to the pulling handle 14 is a generally flat in-moulded lip platform 30. The lip platform 30 providing a base or ledge onto which the upper and lower lips can be placed when in use. The lip platform 30 being generally crescent-shaped when in plan view from above, as best shown in FIG. 1.

As described, the in-moulded lip platform 30 allows for the upper and lower lips to be placed onto the platform 30. This semi-pliable plinth 30 has enough rigidity in to allow the lips to purse and tighten against the platform 30 which has been found to increase the effectiveness of the muscle training methodology described herein.

The pulling handle 14 comprises two parts. The pulling handle 14 being formed having an outwardly projecting arm 32 which extends in a plane normal to the centrally disposed wall 20 and having a first end 32a proximate to the lip platform 30. A grip or elongate grip 34 is positioned orthogonally to the arm 32 at a second end 32b opposite the first end 32a and at the distal end of the device 10, opposite to the panel 12, and connected as a midpoint 34a.

The length of the grip 34 being such that it is purposefully designed for users with reduced movement or arthritic conditions within their hands. The semi-pliable polymer allowing for better or ergonomic location and enabling users to purchase the pulling handle 14 with minimal effort and enabling the device 10 to be placed into the oral cavity with ease and reproducibility.

The skilled person will note that the handle 34 has a downward curvature to it when viewed in side or rear plan view (FIGS. 2 and 3). Again this is for ergonomic reasons and to place the device 10 into the oral cavity in the correct orientation. The pulling handle 14 formed by arm 32 and grip 34, and the lip platform 30, all have a rounded edge 36 which again increases comfort when in use.

In a preferred embodiment, the device 10 is formed from a semi-pliable polymer such as Low-Density Polyethylene (LDPE). This pliable polymer allows the device 10 to deform and mould itself to differing-sized oral cavities and features when in use. Alternatively, the device 10 can be formed from a polymer that is more resilient, and including Polypropylene (PP), High-Density Polyethylene (HDPE), Polyethylene Terephthalate (PET), Polyvinyl Chloride (PVC) or Acrylonitrile Butadiene Styrene (ABS) or blends thereof. Equally, the skilled person will appreciate that the device 10 can be formed from any number of synthetic plastics or rubberised materials, such as a thermoplastic or thermoset material. The above list is no way intended to be limiting or exhaustive.

The device 10 can be manufactured using techniques such as injection moulding, blow moulding, vacuum forming, rotational moulding, compression moulding, rim moulding, powder impression moulding or any other form of plastics or rubber manufacture.

The skilled person will appreciate that different variations or densities of materials could also be provided. The device 10 can be supplied in a number of different colours. By forming the device 10 from a closed cell synthetic plastics or rubberised materials having a smooth surface finish it is very easy for the user to keep the device 10 clean. The device 10 is also supplied with a separate case (not shown) for hygiene reasons. The device 10 and the case can be kept clean with water. The device 10 nor the case react with mouthwashes, and these can also be used to help with cleaning, if preferred.

The moulded device 10 also contains silver ion technology. In order to diminish the risk of the build-up or transfer of germs or bacteria, an antimicrobial additive, such as silver ions, could be admixed with the polymer forming the device 10. Impregnating the device 10 with an antimicrobial additive will prevent against methicillin-resistant *Staphylococcus aureus* (MRSA), *Escherichia coli* (*E. coli*), *Legionella, Salmonella, Cam pylobacter, Listeria* and *Pseudomonas*. Such antimicrobial additives are also proven effective against a wide range of microbes including bacteria, mould and fungi, even multi-drug resistant bacteria and the H1N1 virus. The above list is in no way intended to be limiting and exhaustive.

As silver is inorganic and non-leeching which means that, unlike organic antimicrobial agent technologies, it stays within the item to which it is added.

The use of the present invention will now be described, and it is recommended that the following procedure is followed by a user to obtain the optimum muscle training benefit from the device 10:

1) The muscle toning exercises using the device 10 are easiest to do when the user is seated. The user should try to keep their head facing forward rather than looking up or down.

2) The user grasps the handle 14 and places the plate 12 into their mouth in the correct orientation (with the larger cut-out 26 facing upwards) in front of their teeth but behind but behind their lips.

3) The user then gently closes their mouth such that their lips should be closed (pursed) firmly but their teeth just relaxed in a closed position and not biting tightly. The upper and lower lips should gently rest against the lip platform 30.

4) The user should then gently pull forward on the handle 14, pulling away from their mouth, but keeping their lips tight enough together to prevent the plate 12 from being pulled out of their mouth. The flexible plate 12 will start to deform from the user's teeth and gums. The user is encouraged to pull directly away from their mouth, and not to pull up or down.

5) The user should then pull the handle 14 harder but not so hard as to pull the device 10 out. It should be an effort to keep the device behind the lips, and this is area that the exercise is targeting.

6) The user should hold this position for between 5 to 10 seconds.

7) This exercise should then be repeated three times with several seconds gap in between.

8) It is suggested that this set of three exercises is itself repeated three times each day, leaving at least an hour or two between each set of three.

9) It will take a little time to see improvements, and for some users they may need to use the device 10 for two months. At that point, users find that they can just use the device a few days a week, in order to maintain the desired reduction or complete cessation of snoring.

Without wishing to be limited by a theory, it is understood that the enhanced effect of the oral training device 10 relates to the training the involuntary muscles of the pharynx in the space behind the nose and mouth that connects to the oesophagus.

Users may well notice that in a training session that, as they pull the handle 14 (following steps 4 to 6 above) their tongue hits the back of the pharynx and the tip of the tongue moves towards the lower teeth. The pharynx itself also moves as the muscles work. It is also believed that lip strength plays some role as they strengthen too, since the lips obviously play an important part of mouth and pharynx.

Therefore, the use of the oral training device according to the present invention maximises the pressure applied to the anterior mouth/lip area to produce an enhanced muscle training effect to significantly alleviate or even cure snoring.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in the terms of a means for performing the disclosed function, or a method or process for attaining the disclosed result, as appropriate, separately, or in any combination of such features, can be utilised for realising the invention in diverse forms thereof.

The invention is not intended to be limited to the details of the embodiments described herein, which are described by way of example only. It will be understood that features described in relation to any particular embodiment can be featured in combination with other embodiments.

It is contemplated by the inventor that various substitutions, alterations, and modifications may be made to the invention without departing from the spirit and scope of the invention as defined by the claims.

We claim:

1. An oral training device for muscles of a throat and/or a face of a user, comprising:
    a panel being configured to be received in an oral cavity formed between lips and teeth of the user and having a first face being configured to be adjacent to a lip area of the user, a second face being opposite said first face and configured to be adjacent to the teeth and/or gums of the user when the device is in use, and an outer periphery;
    a handle projecting outwardly from said first face and being configured to apply an outward pulling force to said panel away from the oral cavity of the user when the device is in use; and
    an elongate platform extending laterally across said first face and being configured onto which upper and lower lips of the user are placeable on said elongate platform when the device is in use,
    wherein said panel is divided into three generally flat walls, having a truncated V-shape in plan view from above.

2. The oral training device as claimed in claim 1, wherein said three generally flat walls is comprised of:
    a centrally disposed wall having a first side, a second side opposite said first side and a surface being configured to be proximate to central/lateral incisors in upper and lower jaws of the user when the device is in use;
    a first lateral wall being positioned on one side of said centrally disposed wall and being configured to be proximate to lateral incisors/canine teeth in one side of the upper and lower jaws of the user when the device is in use; and
    a second lateral wall being position on an opposite side of said centrally disposed wall and being configured to be proximate to lateral incisors/canine teeth in an opposite side of the upper and lower jaws of the user when the device is in use.

3. The oral training device as claimed in claim 2, wherein said first lateral wall is offset from said surface of said centrally disposed wall by an angle in a range of 30-40 degrees, and wherein said second lateral wall is offset from said surface of said centrally disposed wall by an angle in a range of 30-40 degrees.

4. The oral training device as claimed in claim 2, wherein said outer periphery corresponding to said centrally disposed wall is comprised of:
    an upper cut-out being configured to receive an upper or superior labial frenulum of the user when the device is in use; and
    a lower cut-out being configured to receive a lower or inferior labial frenulum of the user when the device is in use.

5. The oral training device as claimed in claim 2, wherein said handle comprises:
    an outwardly projecting arm extending in a plane normal to said centrally disposed wall and having a first end proximate to said elongate platform and a second end opposite said first end; and an elongate grip positioned orthogonally to said outwardly projecting arm and connected at a midpoint thereof to said second end of said outwardly projecting arm.

6. The oral training device as claimed in claim 5, wherein said elongate grip has a length at least 1.5 times greater than a width of said first lateral wall.

7. The oral training device as claimed in claim 1, wherein said panel further comprises a generally asymmetrical Booth lemniscate shape, a height, and a width greater than said height.

8. The oral training device as claimed in claim 1, further comprising a peripheral ridge situated around said outer periphery of said panel.

9. The oral training device as claimed in claim 8, wherein said peripheral ridge has a reduced wall thickness between said first face and said second face of said panel.

10. The oral training device as claimed in claim 8, wherein said peripheral ridge is deformable and is configured to seal said panel within the oral cavity of the user when the device is in use.

11. The oral training device as claimed in claim 1, being resiliently deformable and comprised of a semi-pliable polymer material.

12. The oral training device as claimed in claim 1, being integrally formed via injection moulding and/or blow moulding and/or vacuum forming and/or rotational moulding and/or compression moulding and/or rim moulding and/or powder impression moulding and/or any form of plastics or rubber manufacture.

* * * * *